United States Patent [19]
Guzauskas

[11] Patent Number: 6,103,779
[45] Date of Patent: *Aug. 15, 2000

[54] METHOD OF PREPARING MOLDING COMPOSITIONS WITH FIBER REINFORCEMENT AND PRODUCTS OBTAINED THEREFROM

[75] Inventor: Robert Guzauskas, West Palm Beach, Fla.

[73] Assignee: Reinforced Polmers, Inc., Fla.

[ * ] Notice: This patent is subject to a terminal disclaimer.

[21] Appl. No.: 09/176,214

[22] Filed: Oct. 21, 1998

Related U.S. Application Data

[63] Continuation-in-part of application No. 09/070,856, May 5, 1998, abandoned, which is a continuation-in-part of application No. 08/621,723, Mar. 28, 1996, Pat. No. 5,747,553, which is a continuation-in-part of application No. 08/429,139, Apr. 26, 1995, abandoned.

[51] Int. Cl.$^7$ .............................. C08L 1/02; C08L 33/00; C08L 77/10
[52] U.S. Cl. .............................. 523/115; 524/13; 524/35; 524/556; 525/183
[58] Field of Search .............................. 523/115; 524/13, 524/35, 556; 525/183

[56] References Cited

U.S. PATENT DOCUMENTS

| | | | |
|---|---|---|---|
| 4,067,853 | 1/1978 | Schmitt et al. | 523/115 |
| 4,131,597 | 12/1978 | Bluethgen et al. | 523/115 |
| 4,197,643 | 4/1980 | Burstone et al. | 433/420 |
| 4,288,221 | 9/1981 | Engel | 523/115 |
| 4,426,504 | 1/1984 | Nandi | 523/115 |
| 4,433,958 | 2/1984 | Fellman et al. | 523/115 |
| 4,717,341 | 1/1988 | Goldberg et al. | 433/9 |
| 4,718,910 | 1/1988 | Draenert | 523/115 |
| 4,725,631 | 2/1988 | Bastioli et al. | 523/115 |
| 4,894,012 | 1/1990 | Goldberg et al. | 523/115 |
| 4,902,728 | 2/1990 | Pietsch et al. | 523/115 |
| 5,098,304 | 3/1992 | Scharf | 423/215 |
| 5,334,625 | 8/1994 | Ibsen et al. | 523/115 |
| 5,336,699 | 8/1994 | Cooke et al. | 523/115 |
| 5,502,087 | 3/1996 | Tateosian et al. | 523/115 |
| 5,747,553 | 5/1998 | Guzauskas | 523/115 |

OTHER PUBLICATIONS

Kia, Hamid G., "Sheet Molding Compounds Science and Technology", *Sheet Molding Compounds,* Hanser Publishers.

CDA Composites Design & Application, CI's 51st Annual conf. & EXPO '96 Preview Product Awards Competition, p. 14.

Singer, Bruce, "Intracoronal Estetic Splinting," *Compendium,* vol. XVII, No. 5, May 1996, pp. 458–468.

"Summaries of Clinically relevant studies of dental materials from the 1995 meeting of the American Assoc. for Dental Research," *General Denistry*/May–Jun. 1996, pp. 250–257.

Galan et al., "The effect of reinforcing fibres in denture acrylics," *Journal of the Irish Dental Assoc.,* vol. 35, No. 3, pp. 109–113.

A. Lacy, "Adhesive Restoration of a Nonvital Anterior Tooth using a Carbon–Fiber Post and All–Porcelain Crown," *Practical Periodontics and Aesthetic Dentistry,* Sep. 1995, pp. 1–9.

*Primary Examiner*—Nathan M. Nutter
*Attorney, Agent, or Firm*—Millen, White, Zelano & Branigan, P.C.

[57] ABSTRACT

A method of preparing fiber reinforced acrylic thickened compositions which can be molded under low pressures and temperatures to provide thermoset articles, wherein liquid reactive components are slowly absorbed in high molecular weight solid acrylic resin in the form of large particles. The acrylic resin functions as a thickener which delays the viscosity build allowing fiber reinforcement to be incorporated before molding. The molding composition is well suited for use in dentistry and other fields where small amounts or molding composition are used occasionally.

30 Claims, No Drawings

METHOD OF PREPARING MOLDING COMPOSITIONS WITH FIBER REINFORCEMENT AND PRODUCTS OBTAINED THEREFROM

This is a continuation-in-part application of Ser. No. 09/070,856, filed May 5, 1998 and now abandoned, which is a continuation-in-part of Ser. No. 08/621,723, filed on Mar. 28, 1996, now issued as U.S. Pat. No. 5,747,553, which is a continuation-in-part of Ser. No. 08/429,139 filed on Apr. 26, 1995, now abandoned.

FIELD OF THE INVENTION

This invention relates to the preparation of thermosetting molding compositions with an amorphous/non-crystalline acrylic resin thickener, the nature of which permits fiber reinforcement and other additives to be easily incorporated therein. These thermosetting compositions can be dispensed as premixed doughs (bulk molding compounds) or sheets (sheet molding compounds) and can be molded using low pressure molding techniques and conditions (temperature/pressure) to form articles ranging from automotive parts to dental appliances to bathroom shower stalls.

A. Acrylic Resins

Acrylic resins include polymer and copolymer formulations whose major monomeric components belong to two families of esters: acrylates and methacrylates. Acrylics are well known and are commercially available from ICI and others. Trade names such as Elvacite®, Lucite®, Plexiglas®, PERSPEX™ acrylic resins denote these polymer resins. Methyl-methacrylate, ethylacrylate and acrylic acid are common acrylic monomers. Acrylic monomers can polymerize by a free-radical, addition reaction. Two commercially used initiators for free-radical polymerization of acrylic are the peroxide initiator, benzoyl peroxide (BPO) and the aliphatic azonitrile initiator, azobisisobutyronitrile (AIBN). Both BPO and AIBN will decompose into free-radical activators at ambient temperature.

Peroxide initiated polymerizations tend to be more vigorous. Peroxides produce a higher polymerization exotherm which induces polymer chain decomposition with subsequent crosslinking between chain fragments. Crosslinking produces three dimensional network polymers that are said to be thermoset. AIBN and other azonitrile initiators produce lower polymerization exotherms, little polymer chain decomposition, minimal crosslinking and thermoplastic acrylic resins. In addition, azo initiators irreversibly decompose when heated. Therefore, residual azo initiator, AIBN, can be eliminated from acrylic resin by the deliberate heating of the resin.

That acrylic monomers can be polymerized in liquid suspensions using azo initiators such as AIBN is well known. Such azo polymerized vinyl polymers have minimal molecular crosslinking, are thermoplastic and are more or less soluble in various vinyl monomers. Since these thermoplastic vinyl polymers are easily molded using injection molding operations, they are available from commercial manufacturers. But linear thermoplastic vinyl polymers easily absorb surrounding liquids, including water, with resultant swelling and sometimes dissolution. So where absorbed liquids or thermoplasticity may be a problem, crosslinked, thermoset, acrylic polymers are preferable. Most dental appliances are molded of thermoset resin. Thermosetting acrylic resins are the plastic of choice in many industries since the crosslinked polymers resist penetration by many liquids and resist distortion by heat or mechanical stress.

B. Acrylic Thickened Molding Compositions/Doughs

Both suspension and emulsion polymerization processes are used to produce commercial acrylic resins. Suspension polymerization generally produces larger beads of resin while emulsion polymerization generates a very, fine powder. Acrylic beads of linear polymers with their high volume and small surface area are well suited for use in thermoplastic molding processes and equipment, but acrylic powders are typically used in forming acrylic thermosetting molding doughs (bulk molding compounds and sheet molding compounds). Those used in dentistry typically comprise acrylic resin powder, liquid acrylic monomer and an initiator for free-radical polymerization. Thermosetting molding doughs used for industrial applications typically contain a thickener such as an alkali metal oxide. Three types of thermoset dough formulations are commonly used: those incorporating heat activated initiator; those with chemically activated initiator; and those with radiation (light) activated initiator. A mixture of initiators is used in, "dual cure", resins. Dual cures are typically first light initiated, then heat cured.

Industrial molding doughs, also called premix, are prepared and sold as bulk molding compound (BMC) and sheet molding compound (SMC). Industrial mass producers mix perishable doughs at the job site for high volume production runs, or purchase another premix for molding within a few weeks of its preparation. The alkaline earth thickeners, peroxide catalysts and promoters in the dough cause gelation that limits shelf life. Commonly used industrial, alkaline earth thickeners, CaO or MgO, polymerize and build dough viscosity indefinitely.

Thermoset plastic dental fillings, dental crowns and dental prosthesis are most often made by low pressure compression molding of the acrylic dough. To maintain viscosity, the thermosetting acrylic thickened doughs used in dentistry or other small or occasional applications is typically prepared on site due to the short shelf life characteristic.

The thermosetting acrylic molding doughs contain powdered acrylic resin rather than large beads because 1) their rapid solubility in acrylic monomer quickly dissolves the resin into the monomer; and 2) the soluble resin powder contains enough residual initiator to trigger the polymerization of a lightly inhibited monomer liquid. In dental practice, these finely powdered polymers are also of low molecular weight of about 60,000 so as to be readily soluble in the acrylic monomer liquid.

C. Fiber Reinforcement

Although the acrylic doughs provide useful molded articles, the physical properties are not ideal for all applications and have been manipulated by blending methyl methacrylate with other resins, forming copolymers with the methyl methacrylate monomer and/or increasing the degree of crosslinking between polymer chains. Adding fiber reinforcement is desirable for some applications.

Long fibrous fillers, such as glass, carbon, aramid, etc., are known to greatly enhance strength, stiffness and toughness of plastic materials. Long fibers being defined as lengths equal to or exceeding the critical aspect ratio of the fiber matrix combination. Plastics reinforced with such long fibrous inclusions, i.e., composites, exhibit physical and chemical properties that are a composite of the properties of the fibrous fillers and plastic matrix. Typically, the included fiber has tensile strength much higher than the resin matrix, is insoluble in the resin matrix and is chemically, or physically bonded to the resin matrix in such a way as to deflect a crack propagating through the resin matrix along the length of the fiber-matrix interface. Fibers turn the crack, absorb the energy of fracture, reduce the incidence of through-and-through-fracture, and give composites their characteristic properties of high strength, high stiffness, toughness and light weight. The properties of some conventional polymeric materials and composites are disclosed in *CRC Practical Handbook of Materials Science,* Ed. Charles T. Lynch, 1994, pp. 547–548 (vinyls, ASA resins), 327–328 (glass fiber, organic fiber) and 342 (organic matrix composites). While the use of long fibrous fillers can provide advantageous physical properties, fiber is difficult to incorporate into a resin matrix, particularly where the matrix resin is highly viscous.

The thermosetting acrylic thickened doughs of powdered, low molecular weight acrylic resin and lightly inhibited acrylic monomer liquid are highly viscous. The mixture quickly passes from a wet slurry, to a viscous paste and then to a moldable dough as the resin particles first absorb and then dissolve in the monomer. Unfortunately, this otherwise convenient, rapid transition from slurry to paste to dough produces a very abrupt rise in viscosity. In addition, residual BPO initiator in the acrylic resin powder, intended to thermoset the mix, begins spontaneous decomposition, initiates polymerization and can reduce the shelf life of the fresh dough to only a few hours at 80° F.

Early efforts to bring a thermoset, fiber reinforced, organic polymer composite to the dental market have foundered on the two problems of 1) prematurely high viscosity; and 2) premature gelation (polymerization). Viscosity is intentionally built-up rapidly in dental acrylic as finely powdered, low molecular weight resins are dissolved in monomer to make a moldable dough. Premature gelation is a consequence of the demand for low curing temperature. Adding reinforcing fibers to this increasingly viscous mix quickly becomes impractical. Adding long fibers to any liquid typically causes the liquid to become intractably thick, even at levels of only 2 wt. %. As disclosed by J. E. Gordon in *The New Science of Strong Materials,* 2nd Ed., p. 177, Princeton Univ. Press, "Beyond two percent, therefore, it is impossible to add fibers to a matrix and it becomes necessary to add the matrix to the fibers." Prolonged mixing with significant energy input and subsequent heat build up is required to incorporate fibers into liquid monomer and wet the fiber reinforcement.

Dental researchers have long wrestled with the problem of incorporating reinforcing fibers into thermoset, molding doughs. For example, Ladizesky, Chow and Cheng, using a cloth, impregnated with acrylic syrup, disclose, "The added technical procedure to construct the (fiber) reinforced dentures required an additional two hours (20%) of the standard laboratory time." *Denture Base Reinforcement Using Woven Polyethylene Fiber,* International Journal of Prosthodontics, Vol. 7, No. 4, p. 307–314 (1994). Targis® by Ivoclar is an example of a commercial pre-preg used in dentistry.

In the 1960's, Bowen, U.S. Pat. No. 3,066,112, incorporated particulate glass fillers into acrylic and vinyl ester resins used as dental fillings. Since then, small particulate fillers have been used to reduce the shrinkage of polymerization, increase hardness and improve abrasion resistance of these dental materials. However, these particle filled materials do not behave as fiber reinforced composites. Unless the critical aspect ratio, length/diameter, of a reinforcing fiber embedded in a resin matrix is equaled or exceeded, the composite material fails at low stress levels. Early dental composites did not contain particulate fillers with aspect ratios exceeding 4/1. In dental practice, particulate fillers are nearly spherical to enhance flow and mixing. Consequently, there is very little resistance to crack propagation in these composites. The result is very little enhancement in strength, stiffness and toughness of the dental composite material. Short particle fillers can actually make the dental materials brittle.

Fiber reinforcement has been incorporated in thermosetting molding doughs on an industrial scale and fiber reinforced industrial molding doughs are available as bulk molding compound (BMC) or sheet molding compound (SMC). However, these compounds have extremely high viscosities of 20–30 million centipoise. These high viscosities are manageable on the industrial scale where large hydraulic or electric presses can be used to generate the high molding pressures and temperatures necessary to mold these compounds. It is desirable to reduce these pressure and temperature requirements to enable molding of fiber reinforced resins under low pressure molding conditions.

Short shelf life, high molding pressure and temperature requirements have prevented the commercial production and distribution of fiber reinforced, polyester/acrylic, vinyl ester and acrylic, molding doughs to the very small user doing an occasional or opportunistic molding. Perishable, industrial BMC and SMC has, until now, been unsuitable for the small batches of premix used on the occasional, very small job of the dentist, the auto body mechanic, the boat repair person or the like. The small of occasional user, like the dentist, requires a dough moldable with manual pressure, curable at hot water temperatures and with a long shelf life at ambient temperature for their opportunistic type of work.

The use of additives to reduce the viscosity of the molding dough for low pressure molding has had limited success. See: *Proceedings, Composites Institute 51st Annual Conference and Expo 96.* A low melting crystalline polyester resin available under the tradename CRYSTIG™ polyester resin, imparts low pressure qualities to the molding dough/composition when melted at a temperature of over 100° C. and subsequently cures. This requires the reinforcement be incorporated in the melt just before use. It is desirable to provide a fiber reinforced thermosetting molding dough which is not so limited.

Three factors prevent the easy, on site mixing of resin powders and reinforcing fibers, with curable liquid monomers.

1) Resin particles and fibers tend to separate into layers and clumps, called agglomeration, and require periodic stirring to prevent this separation.
2) Prolonged mixing is required to incorporate particles and fibers into liquid monomer and thoroughly wet the particulate fillers and fiber reinforcement. If the resin particles dissolve immediately, viscosity build up prevents farther mixing.
3) Dry ingredients must be very dry. Water contaminated powder and fiber will contaminate and weaken the composite. Surface moisture, adsorbed at ambient temperature, must be removed from particles and fibers so the monomer can wet and bond to these ingredients. Interfacial bonding between solid fillers and curable liquids must occur during polymerization if physical properties are to be enhanced rather than degraded in the composite.

Drying and mixing require time and special equipment not available to the opportunistic molder working at the occasional job.

SUMMARY OF THE INVENTION

It is an object of this invention to provide fiber reinforced thermosetting bulk molding compounds (BMC) and sheet molding compounds (SMC) and precursors thereto with extended shelf stability.

It is another object of this invention to provide a thickener for thermosetting molding compositions (BMC, SMC) which delays viscosity build-up to provide an opportunity to incorporate long fiber reinforcement and employ low pressure molding techniques without heating.

It is another object of this invention to provide a thickener for thermosetting molding compositions which thickens by a physical mechanism and not a chemical mechanism, and participates in the cure.

It is another object of this invention to provide thermosetting molding compositions, precursors thereto and methods for their preparation, which allow long fiber reinforcement to be easily incorporated therein.

It is another object of this invention to provide fiber reinforced thermosetting bulk molding compounds (BMC) and sheet molding compounds (SMC) and precursors thereto which can be molded under the pressures and temperatures of low pressure molding equipment.

It is an another object of the present invention to provide a thermosetting acrylic thickened composition with fiber reinforcement suitable for industrial applications or dental appliances with fiber reinforcement that enhances the physical properties of the molded product.

It is another object of the present invention to provide a thermosetting molding composition suitable for dental appliances which forms composites of suitable strength to replace the metal frameworks and superstructure employed to reinforce and support dental crowns and fixed and removable dental bridge work.

It is a another object of the present invention to provide a thermosetting molding composition with fiber reinforcement which forms dental appliances of suitable strength to replace those produced by lost-wax casting and ceramic build-ups, with reduced fabrication time.

It is another object of the present invention to provide a thermosetting premixed acrylic-based molding composition with fiber reinforcement suitable for industrial applications or dental appliances to reduce exposure of the operator (and patient) to hazardous vapors.

It is another object of the present invention to provide a thermosetting molding composition which has an extended shelf life so as to reduce waste.

It is an additional object of the present invention is to provide a thermosetting molding composition which experiences less shrinkage upon cure, requiring fewer adjustments (secondary finishing), to complete the part.

It is a further object of the present invention to provide a thermosetting molding composition with long fiber reinforcement which is compatible with existing techniques, equipment and procedures for producing dental appliances.

These and other objects are achieved through the methods and compositions of this invention which comprises molding compositions and precursors thereto. This includes bulk molding compositions and sheet molding compositions. BMC and SMC are composed basically of four principle ingredients: thermosetting resins (polymerizable resin solution), fibers, optionally fillers and additives. With this overall combination in place, it is feasible to use various types of specific ingredients to meet the required properties of the final product, and that makes BMC and SMC very versatile reinforced composites with an almost indefinite number of possible formulations. A general formula of typical sheet molding and bulk molding compounds, employing a variety of free radical initiators and other ingredients, which can be used in the method of thickening polymerizable resin solutions into moldable compositions provided by this invention follows.

Suitable polymerizable resin solutions are made by dissolving a curable resin polymer, in a curable monomer, oligomer or polymer solvent, as a means of making a curable molding composition, e.g.:

a) acrylic resins dissolved in a polymerizable monomer solvent, the polymerizable monomer solvent dissolving both the acrylic resin and "the thickener", examples of the polymerizable monomer solvent include styrene monomer, acrylic monomer, EGDMA (ethylene glycol dimethacrylate), TEGDMA (triethylene glycol dimethacrylate), UEDMA (urethane dimethacrylate) or similar acrylates;

b) polyester resins dissolved in a polymerizable monomer solvent, said polymerizable monomer solvent dissolves both the polyester resin and "the thickener", e.g., styrene monomer, acrylic monomer, EGDMA, TEGDMA, UEDMA or similar acrylates;

c) styrenic resins dissolved in a polymerizable monomer solvent, said polymerizable solvent dissolving both the styrenic resin and "the thickener", e.g., styrene monomer, acrylic monomer, EGDMA, TEGDMA, UEDMA or similar acrylates; and d) vinyl ester resins dissolved in polymerizable monomer solvent, said polymerizable solvent dissolving both the vinyl ester resin and "the thickener," e.g., styrene monomer, acrylic monomer, EGDMA, TEGDMA, UEDMA or similar acrylates.

The addition of fiber(s) provides a means for strengthening or stiffening the polymerized resin solution. The fiber(s) often used are:

1) inorganic crystals or polymers, e.g., fibrous glass, quartz fibers, silica fibers, fibrous ceramics, e.g., alumina-silica (refractory ceramic fibers); boron fibers, silicon carbide whiskers or monofilament, metal oxide fibers, including alumina-boria-silica, alumina-chromia-silica, zirconia-silica, and others;

2) organic polymer fibers, e.g., fibrous carbon, fibrous graphite, acetates, acrylics (including acrylonitriles), aliphatic polyamides (e.g., nylons), aromatic polyamides, olefins (e.g., polypropylenes, polyesters, UHMW polyethylenes), polyurethanes (e.g., spandex, alpha-cellulose, cellulose, regenerated cellulose (e.g., rayon), jutes, sisals, vinyl chlorides (e.g., nylon), vinyl chlorides (e.g., vinyon), vinyldienes (e.g., saran), flax and thermoplastic fibers;

3) metal fibers, e.g., aluminum, boron, bronze, chromium, nickel, stainless steel, titanium or their alloys; and 4) "Whiskers", single, inorganic crystals.

Suitable nonfibrous filler(s) are inert, particulate additives being essentially a means of reducing the cost of the final product, which often reduce some physical properties of the polymerized, resin-fiber composite and are optional. Examples include calcium carbonates of various forms and origins, silica of various forms and origins, silicates, silicon dioxides of various forms and origins, clays of various forms and origins, feldspar, kaolin, flax, zirconia, calcium sulfates, micas, talcs, wood in various forms, glass (milled, platelets, spheres, micro-balloons), plastics (milled, platelets, spheres, micro-balloons), recycled polymer composite particles, metals in various forms, metallic oxides or hydroxides (except those that alter shelf life or viscosity), metal hydrides or metal hydrates, carbon particles or granules, alumina, tabular, aluminum powder, aramid, bronze, carbon black, carbon fiber, cellulose, alpha cellulose, coal (powdered), cotton, fibrous glass, graphite, jute, molybdenum, disulfide, nylon, orlon, rayon, silica, amorphous, sisal fibers, fluorocarbons and wood flour.

Suitable additives include initiators and thickener(s). Initiators are the means of generating the free radicals that begin and sustain polymerization. Said initiator-monomer combination, otherwise stable for at least a week at ambient temperature, is activated by means of elevating temperature, or by exposing to microwave, infrared, visible, ultra-violet or shorter radiations thus generating free radicals. Specific initiators are described below.

Acrylic beads are used as the means of thickening the polymerizable resin solution into a moldable dough. Said solid acrylic beads being of an essentially linear, acrylic polymer act by slowly absorbing the polymerizable monomer resin solvent. The solid, acrylic bead thickeners are essentially free of initiators as a means to extend shelf life. These acrylic bead thickeners are of a molecular weight, chemical composition and large bead diameter as a means to be both slowly dissolving in and highly absorbing of the polymerizable monomer, oligomer or polymer solvent.

The following are functional additives and a means of imparting desirable properties to the molding composition or to the cured composite. These include, but are not limited to, anti-blocking agents, anti-caking agents, anti-foaming agents, antioxidants, anti-slip agents, anti-static agents, blowing agents, coupling agents, compatibilizers, dispersing aids, flatting agents, inhibitors, catalysts, accelerators/promoters, heat stabilizers, light stabilizers, wetting agents, plasticizers, extenders, thixotropics, flame, fire and smoke retarders, internal mold releases, lubricants, impact modifiers, tougheners, coloring/dyes/pigments, odorants and deodorants, low profile or low shrink additives, low pressure additives, clarifying agents, opacifiers, thickeners, viscosity control agents, permeability modifiers, solvents, waxes and thermoplastics.

The molding compositions preferably comprise:

a) a liquid monomer, oligomer, polymer or combination thereof, containing vinyl unsaturation, which polymerizes in the presence of an activated free-radical polymerization initiator;

b) at least 35 wt. %, based on the total weight of liquid monomer, oligomer, polymer or combination thereof containing vinyl unsaturation in the composition, of a solid acrylic resin which is soluble in said liquid monomer, liquid oligomer, liquid polymer or combination thereof containing vinyl unsaturation, having an average particle size in the range of 0.005 mm to 0.5 mm with at least a portion of said liquid monomer, oligomer, polymer or combination thereof containing vinyl unsaturation, absorbed therein, said solid acrylic resin is free of active free-radical polymerization initiators and reacts with the liquid monomer, oligomers, polymers and combinations thereof, absorbed therein in the presence of an activated free-radical polymerization initiator;

c) at least 10 wt. %, based on the total weight of the composition, of long fiber reinforcement having an aspect ratio (L/D) greater than 5:1 and an average length of at least 0.25 mm which is insoluble in the solid acrylic resin; and d) a free-radical polymerization initiator, the activity of which can be restrained under ambient conditions or is inactive at ambient temperature so as to provide a shelf life of at least one month at ambient temperature. The molding compositions are free of alkali earth metal oxide fillers/thickeners.

The precursors to a molding composition comprise:

a) a thermosetting resin in solution of a curable liquid monomer, liquid oligomer, liquid polymer or combination thereof containing vinyl unsaturation, which polymerizes in the presence of an activated free-radical polymerization initiator;

b) about 35 wt. %, based on the total weight percent of the liquid monomer, oligomer, polymer or combination thereof in the composition, of a solid acrylic resin which is soluble in said liquid monomer, oligomer, polymer or combination thereof containing vinyl unsaturation, which has an average particle size in the range of 0.005 mm to 0.5 mm, with at least a portion of said liquid monomer, oligomer, polymer or combination thereof containing vinyl unsaturation absorbed therein and which is free of free-radical polymerization initiators; and c) at least 10 wt. %, based on the total weight of the composition, of long fiber reinforcement having an aspect ratio (L/D) greater than 5:1 and an average length of at least 0.25 mm.

The precursor compositions are shelf stable for at least one month and are free of alkali earth metal oxide fillers/thickeners and active free-radical initiators.

The methods comprise:

a) mixing a solid acrylic resin, which is free of active free-radical polymerization initiators, with
  (i) one or more liquid monomers, liquid oligomers, liquid polymers or a combination thereof with vinyl unsaturation which polymerizes in the presence of an activated free-radical polymerization initiator, wherein said solid acrylic resin absorbs the liquid monomers, liquid oligomers, liquid polymers or combination thereof containing vinyl unsaturation, and reacts with said liquid monomers, liquid oligomers, liquid polymers and combinations thereof, absorbed therein, in the presence of an activated free-radical polymerization initiator; and
  (ii) long fiber reinforcement having an aspect ratio L/D greater than 5:1, which is insoluble in said solid acrylic resin; and b) aging the mixture of solid acrylic resin, liquid monomer, liquid oligomer, liquid polymer or combination thereof containing vinyl unsaturation, and long fiber reinforcement for at least 24 hours to allow absorption of the liquid monomer, oligomer, polymer or combination thereof, by the solid acrylic resin.

This invention involves the preparation of novel compositions of stable, thermosetting, acrylic, styrenic, vinyl ester or polyester thickened doughs. Preferred embodiments of these compositions can be compounded to be compression molded at low pressure such as that from the manual screw or small hydraulic press familiar to a dental laboratory or low pressure molding equivalents. The preferred compositions can be cured at low temperatures using a hot water bath or UV or visible light source familiar to a dental laboratory. These compositions include a highly absorbent, solid acrylic resin which functions as a thickener and allows the economic, bulk manufacture and packaging of fiber reinforced polyester, vinyl ester, styrenic or acrylic thickened compositions. This same highly absorbent, solid acrylic resin allows a later distribution of the small quantities of these molding compositions to users remote in time and place from their site of manufacture.

The fiber reinforced acrylic, vinyl ester/acrylic and polyester/acrylic have a combination of sufficiently:

1) long shelf life;

2) low molding pressure; and 3) low curing temperature to be practical for the dentist or, the low production volume, custom molder, or the occasional molder at the opportunistic job.

The thickening agent is preferably a solid soluble, highly absorbent, high molecular weight and unbranched thermoplastic acrylic resin. This thickener defeats the problems of:

1) Rapid viscosity build up during mixing of ingredients which prevents the thorough mixing and wetting of fillers and fibers by the liquid; and 2) Premature dough gelation.

The slowly soluble solid acrylic resin allows prolonged mixing of fiber, filler and liquid ingredients for periods as long as one hour. The slow dissolution of the solid acrylic resin delays viscosity build up for a length of time required to thoroughly mix and wet reinforcing fibers in the premix slurry. This unique acrylic resin thickening agent can act entirely without alkaline earth additives. During a period of maturation, typically 1–4 days, the solid acrylic resin absorbs the monomer solvent and dissolves to form a curable dough. This period of maturation allows the thickener to convert the wet slurry first into a paste and then into a dough. This dough can remain moldable at a low pressure for many months and as long as two years when totally devoid of unstable initiators of polymerization such as benzoyl peroxide or azo initiators. Since the solid acrylic resin thickener is devoid of active initiators, stable initiators such as t-butyl peroxybenzoate and inhibitors can be incorporated into the molding compositions to avoid premature gelation of the dough. This facilitates a long shelf life.

The preferred acrylic resin thickener is an unbranched polymethyl methacrylate resin (PMMA) polymerized with an azo initiator in a suspension polymerization to a molecular weight of about 400,000 as determined by GPC using a conventional solvent for PMMA resins in about 0.1 mm particles/beads. An amount of 0.25 grams of a 400,000 molecular weight polymer dissolved in 50 ml of methylene chloride measured at 20° C. using a No. 50 Cannon-Fenske viscometer has an inherent viscosity of 1.25. These resins are commercially available from ICI Chemical under the tradename Elvacite® 2051.

This preferred thickening agent, a thermoplastic, solid acrylic resin, is created by raising the temperature of the resin above the decomposition temperature of the azo initiators to eliminate residual initiator. This can be done in the autoclave immediately following suspension polymerization. Or, the resin particles/beads can be baked at up to 100° C. Either method decomposes and eliminates residual azo initiator. Baking may cause the particles/beads to stick together in aggregates. The baked particle/bead aggregate can be tumbled in a drum mixer for 30 minutes to break up clumps of resin beads. Preferably the polymer is baked at a temperature above the decomposition temperature of the azo initiator but below the polymer's glass transition temperature to avoid resin fusion.

A large particle/bead size minimizes the soluble exposed surface area and a very large high molecular weight minimizes polymer solubility. Various combinations of bead size and molecular weight make the beads more or less soluble during compounding. It's relative insolubility allows the resin to mix with a liquid monomer, oligomer or polymer, preferably methyl methacrylate, without producing a noticeable immediate increase in viscosity. The preferred thickening agent slowly absorbs the liquid, swells and dissolves during a one to four day maturation period in a sealed container at 70° F. The incubator is inverted at least once every 24 hours. During this maturation period, the viscosity of the wet slurry increases to a paste and then plateaus at a doughy consistency having more or less tack and viscosity depending on the nature and the ratios of liquid to solid ingredients.

With long fiber reinforcement incorporated therein, the molding composition provides thermoset articles, including dental appliances, which are composites with a unique property profile. These composites can substitute the metal frameworks and superstructure used to support dental crowns and bridge work. These composites also provide an alternative to ceramic build-ups and appliances made by lost wax casting. In addition to enhancing physical properties, the fiber reinforcement reduces shrinkage in the molded article, requiring fewer adjustments and finishing steps.

The relatively long shelf-life of the molding compositions of the present invention of at least one week provides adequate time to uniformly blend in the fiber reinforcement, even where mixing for extended periods of over one hour is required. Where the shelf-life extends beyond one year, premixes can be prepared and waste is reduced. The extended shelf life is determined by the initiator and the additives utilized. Preferably, benzoyl peroxide catalyst is avoided, unless its activity at ambient temperature is suppressed, and the use of alkali metal oxide fillers to thicken the formulation is avoided.

The term "acrylic resins" as used herein is intended to include acrylic monomers of the structure:

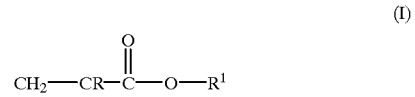

(I)

wherein R=H or a hydrocarbon based radical, and
$R^1$=a hydrocarbon based radical;
and oligomers, polymers and copolymers thereof. Included within the acrylic polymers are linear, branched and crosslinked homopolymers. Included within the acrylic copolymers are graft copolymers, random copolymers, block copolymers and crosslinked copolymers with two or more acrylate monomers of formula I or different monomers such as styrene and acrylonitrile (ASA resins) and acrylamide and methacrylamide. The preferred acrylic resins are the monomers, polymers and copolymers, both linear and crosslinked, of methylmethacrylate and ethylmethacrylate. Suitable comonomers include amino methacrylates available from Creanova such as N,N-Dimethylamineothyl Methacrylate, N-Dimethylaminopropyl Methacrylamid, and 2-ter.-Butylamineothyl Methacrylate.

The hydrocarbon based radicals of R and $R^1$ include methyl, ethyl, propyl, isopropyl, and n-butyl, sec-butyl, isobutyl, tert-butyl, hexyl, heptyl, 2-heptyl, 2-ethylhexyl, 2-ethylbutyl, dodecyl, hexadecyl, 2-ethoxyethyl isobornyl and cyclohexyl. Preferred acrylates have R and $R^1$ selected from the $C_1$–$C_4$ series. The most preferred acrylic polymer is based on methylmethacrylate. A preferred methylmethacrylate acrylic polymer is Elvacite® 2051, available from ICI. Other examples include those provided by Creanova Inc. such as methacrylic acid, Ethyl Methacrylate, n-Butyl Methacrylate, Iso-Butyl Methacrylate, Stearly Methacrylate, Cyclohexyl Methacrylate, 2-Ethylhexyl Methacrylate, Methacrylic Ester, Lauryl Methacrylate, n-Hexyl Methacrylate, Isobornyl Methacrylate, Benzyl Methacrylate, Allyl Methacrylate, 3,3,5-Trimethyl-Cyclohexyl Methacrylate, 1,4-Butanediol Dimethacrylate, 1,3-Butanediol Dimethacrylate, 1-3,-Butanediol Dimethacrylate, Polyethylene Glycol Dimethacrylate, Triethylene Glycol Dimethacrylate, Diethylene Glycol Dimethacrylate, 1,6-Hexanediol Dimethacrylate, Tetratethylene Glycol Dimethacrylate, Trimethylolpropane Trimethacrylate, Timethylolpropane Trimethacrylate, 1,1 2-Dodecanediol Dimethacrylate, Glycerol-1,3-Dimethacrylate, Diurethane Dimethacrylate, 2-Hydroxyethyl Acrylate, Hydroxypropyl Acrylate, 2-Hydroxyethyl Methacrylate, and Glycerolmonomethacrylate. The acrylic resins often have polmerization inhibitors such as methlethyl hydroquinone incorporated in amounts less than 0.1%.

The term "acrylic resins" as used herein is also intended to include vinyl ester resins such as those derived from Bis-GMA. Bis-GMA is essentially an oligomer of the formula

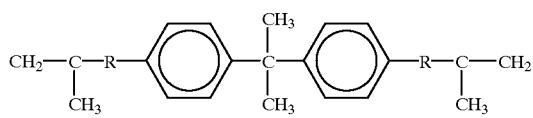

wherein R is

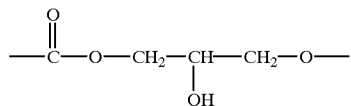

which can be obtained by reaction of one molecule of bisphenol-A and 2 molecules of glycidylmethacrylate or by reaction of diglycidylether of bisphenol-A with methacrylic acid. Similar vinyl esters can be prepared using other polyepoxides and unsaturated monocarboxylic acids. These resins are cured at ambient or elevated temperatures by free-radical polymerization in a manner analogous to the acrylic resins containing monomers of formula (I) above.

The term "solid acrylic resin" as used herein is intended to include polymers and copolymers of the acrylate monomers described above and polymers produced from Bis-GMA described above.

The compositions of this invention include a liquid monomer, liquid oligomer or liquid polymer with vinyl unsaturation which cures to a thermoset polymer in the presence of a free-radical polymerization initiator. The liquid monomer oligomer or polymer must also be able to solubilize the solid acrylic resin so that the liquid monomer, oligomer or polymer will be absorbed by the solid acrylic resin. Suitable liquid monomers, oligomers and polymers include the liquid acrylic monomers described above and liquid oligomers (diacrylates and dimethacrylates) and polymers obtained therefrom. Suitable liquid oligomers and polymers also include the liquid Bis-GMA oligomers and polymers described above and further include liquid polyester resins, liquid carboxylated acrylates, liquid carboxylated methacrylates, liquid styrene monomers liquid substituted styrene monomers and oligomers. Examples of dimethacrylates include ethylene glycol dimethacrylate (EGDMA), triethylene glycol dimethacrylate (TEGDMA) and urethane dimethacrylate (UEDMA).

The compositions of this invention contain at least a portion of solid acrylic resin, preferably about 35 wt. %, most preferably 35–70 wt. % of the total weight percent of the liquid monomer, oligomer, polymer or combination thereof in the composition. The solid acrylic resin functions as a highly absorbent thickener which participates in the cure. Suitable solids are sold under the trade name Elvacite® 2051 by ICI. This highly absorbent solid acrylic resin is amorphous and thermoplastic and preferably a linear and unbranched homopolymer. The solid acrylic resin preferably has 1) a high molecular weight, preferably above 100,000, most preferably about 400,000 as determined by conventional gel permeation chromatography (GPC) methods using conventional solvents for acrylic resins, such as methylene chloride; 2) a large particle size, preferably about 0.005 mm to 0.1 mm and most preferably about 0.1 mm; and 3) essentially no active free-radical polymerization initiators. The solid acrylic resin preferably has an inherent viscosity of about 1.25 as tested in a Cannon-Fenske viscometer with 0.25 grams in 50 ml of methylene chloride at 20° C.

The solid acrylic resin absorbs solvent which in the composition of the invention is the liquid monomer, oligomer or polymer. The function of this solid acrylic resin within the molding composition is to provide a delayed viscosity build, thus permitting the prolonged mixing necessary to incorporate thoroughly wet high volumes of filler and fiber into the molding composition. Absorption of the liquid monomer, oligomer or polymer is preferably not substantially complete until at least 2 hours after being mixed with the solid acrylic resin. Most preferably, absorption of the liquid monomer, oligomer or polymer by the solid acrylic resin (viscosity build) is substantially complete (about 90%) within 1 to 4 days from forming a mixture thereof.

The delayed absorption of the liquid provides for a low viscosity which is sufficiently low to enable both molding compounds and sheet molding compounds to be molded under the temperatures and pressures of low pressure equipment.

The amount of acrylic resin (acrylics and vinyl esters) within the compositions of this invention can vary widely, particularly when employed with other compatible resins. The amount of acrylic resin (liquid and solid) preferably ranges from 35 to 95 wt. % of the liquid monomers, oligomers and/or polymers in the composition, more preferably from about 50–70 wt. % of these liquid components in the composition. Acrylic resins can form 100% of resin component of the composition except where vinyl ester resin is the "acrylic resin".

The compositions of the present invention can include other solid or liquid resins which will participate in the free-radical polymerization or solid resins which remain inert during polymerization, functioning as organic fillers or other additive. Essentially any liquid or solid vinyl or diene containing monomer, oligomer, polymer or copolymer which will participate in free-radical polymerization at ambient temperature can be used. These include polyesters and those derived from the monomers selected from the group consisting of vinyl ethers, acrylonitrile, styrene, propylene, vinyl acetate, vinyl alcohol, vinyl chloride, vinyldiene chloride, butadiene, isobutylene, isoprene, divinylbenzene and mixtures thereof. An example of an inert resin is polyethylene, which in particulate form can function as an organic filler. However, it is preferable that acrylic resins, i.e., those derived from the monomers of formula 1 and the vinyl ester resins be used exclusively in the molding compositions of this invention. Examples of suitable solid acrylic resins are methacrylate polymers under the trademark ROHAGUM®, ROHAMERE® and ROHADON® available from Creanova.

Embodiments of this invention include thermosetting molding compositions and precursors thereto. The thermosetting molding compositions of the present invention include a free-radical polymerization initiator. This initiator can be any conventional free-radical initiator. The initiator preferably has an activity which can be restrained (inhibited/retarded), preferably at ambient conditions and most preferably elevated temperatures. Free-radical initiators which initiate polymerization by exposure to either elevated temperatures above ambient temperature and/or exposure to UV or visible light are well suited for providing molding compositions with the requisite shelf stability of at least one week. Suitable temperature activated initiators include t-butyl peroxybenzoate, sold under the trade name Trigonox® by Akzo Chemicals Inc., t-butyl hydro-peroxide and the peroxy ketals, also available from Akzo Chemicals Inc. and the VAZO catalysts such as VAZO-88™1,1-azobi (cyclohexane carbonitrile) available from DuPont. Other suitable initiators include ketone peroxides, alkyl peroxides, aryl peroxides, peroxy esters, perketals, peroxydicarbonates, alkylhydroperoxides, diacyl peroxides, VAZO compounds, photoinitiators and heat labile photoinitiators.

Examples of ketone peroxides include methyl ethyl ketone peroxide, methyl isobutyl ketone peroxide, acetyl acetone peroxide and cyclohexanone peroxide.

Examples of alkyl peroxides and aryl peroxides include dicumyl peroxide, tert.butylcumyl peroxide, di-tert.amyl peroxide, 1,3-di(2-tert.butylperoxy isopropyl)benzene, di-tert.butyl peroxide, 2,5-dimethyl 2,5-di(tert.butylperoxy) hexane, 2,5-dimethyl 2,5-di(tert.butylperoxy)hexane, dibenzoyl peroxide, tert.butyl 3-isopropenylcumyl peroxide, 1,4-di(2-tert.butylperoxy isopropyl)benzene, 1,4-di(2-neodecanoyl peroxy isopropyl)benzene, di(1-hydroxycyclohexyl) peroxide, diisobutyryl peroxide, dioctananoyl peroxide, didecanoyl peroxide and 2,2-Bis(4,4-di(tert.butylperoxy-cyclohexyl)propane.

Examples of peroxyesters include tert-butyl peroxy-2-ethylhexanoate (Trigonox 21), tert-amyl peroxy-2-ethylhexanoate (Trigonox 121), tert-butyl peroxy-3,5,5-trimethylhexanoate (Trigonox 42S), tert-butylperoxy-2-methylbenzoate (Trigonox 97-C75), 2,5-dimethyl 2,5-di (benzoylperoxy)hexane (AZTEC), 2,5-dimethyl-2,5-di-(2-ethyl-hexanoylperoxy)hexane (Trigonox 141), tert-butyl peroxy-isopropyl carbonate (Trigonox BPIC), tert-butyl peroxy-stearyl carbonate, tert.-butyl peroxyacetate, tert.-amyl peroxyacetate, tert.-butyl peroxypivalate, tert.-amyl peroxypivalate, tert.-butyl peroxyneodecanoate, tert.-amyl peroxyneodecanoate, tert.-butyl peroxybenzoate, tert.-amyl peroxybenzoate (Trigonox 127), tertiary-butyl peroxy 2-ethylhexyl carbonate, tertiary-amyl peroxy 2-ethylhexyl carbonate, cumyl peroxyneodecanoate, cumyl peroxyneoheptanoate, tertiary-butyl peroxyneoheptanoate, tertiary-butyl peroxyisobutyrate, tertiary-butyl monoperoxy maleate and tert.-butyl peroxydiethyl acetate.

Examples of perketals include 1,1-di(t-amylperoxy) cyclohexane (USP-90MD) 2,2,-di(tert.butylperoxy)butane, n-butyl 4,4-di(tert.butylperoxy)valerate ethyl 3,3-di (tert.butylperoxy)butyrate, 3,3,6,6,9,9-hexamethyl 1,2,4,5-tetraoxa cyclononane, 1,1-di-(tert-butylperoxy)-3,3,5-trimethylcyclohexane, 1,1-di-(tert-butylperoxy)cyclohexane and di-tert.-butyldiperoxyazelate.

Examples of peroxy dicarbonates include di-(sec-butyl) peroxydicarbonate, di-(n-butyl)peroxydicarbonate, di-(2-ethylhexyl)peroxydicarbonate di-(4-tert-butylcyclohexyl) peroxydicarbonate, dicyclohexyl peroxydicarbonate, dimyristyl peroxydicarbonate and dicetyl peroxydicarbonate.

Examples of alkylhydroperoxides include cumene hydroperoxide, 1,4-di(2-hydroperoxy isopropyl)benzene, tert.amyl hydroperoxide tert.butyl hydroperoxide, 2,4,4-trimethylpentyl-2 hydroperoxide and diisopropylbenzene monohydroperoxide Examples of diacyl peroxides include acetyl cyclohexane sulphonyl peroxide, di(2,4-dichlorobenzoyl)peroxide, di(3,5,5-trimethyl hexanoyl)peroxide dilauroyl peroxide, disuccinic acid peroxide and di(4-methylbenzoyl)peroxide.

Examples of VAZO compounds include 2,2'-azobis(2,4-dimethylpentanenitrile), 2,2'-azobis(2,4-dimethylvaleronitrile) (Vazo® 51), 2,2'-azobis(2-methylpropanenitrile), 2,2'-azobis(isobutyronitrile) (Vazo® 64), 2,2'-azobis(methylbutanenitrile), 2,2'-azobis (methylbutyronitrile) (Vazo® 67), 1,1'-azobis (cyclohexanecarbonitrile) or 1,1'-azobis(cyanocyclohexane) (Vazo® 88)

Examples of photoinitiators include 2-butoxy-1,2-diphenylethanone, 2,2-dimethoxy-1,2-diphenylethanone, a mixture of oligo(2-hydroxy-2-methyl-1-(4-(1-methylvinyl) phenyl)propanone)+2-hydroxy-2-methyl-1-phenyl-1-propanone, oligo(2-hydroxy-2-methyl-1-(4-(1-methylvinyl) phenyl)propanone), a mixture of 2,4,6-trimethylbenzophenone+4-methylbenzophenone+oligo(2-hydroxy-2 methyl-1-(4-(1-methylvinyl)phenyl) propanone), a mixture of oligo(2-hydroxy-2-methyl-1-(4-(1-methylvinyl)phenyl)propanone)+2-hydroxy-2-methylphenyl 1-propanone, 2,4,6-trimethylbenzoyldiphenylphosphine oxide+methylbenzylphenone, a mixture of 2,4,6-trimethylbenzophenone+4-methylbenzophenone, a mixture of 2-isopropylthioxanthone, ethyl 4-(dimethylamino) benzoate and methyl-benzophenone, benzophenone and diaryl iodonium hexafluoroantiomonate Examples of miscellaneous initiators include triaryl sulfonium hexafluorophosphate+propylene carbonate and triaryl sulfonium hexafluoroantimonate+propylene carbonate.

To obtain stable mixtures, the initiator should be compatible with the acrylic resin and preferably, the acrylic resin is inhibited with the methyl ether of hydroquinone. Preferred curing initiators (and inhibitors) provide a-formulation which remains stable for months, preferably at least from six months to one year, preferably in excess of two years. Such curing initiators are typically heat activated at temperatures well above ambient temperature and more typically above 75° C. An example of a preferred free-radical initiator which can be activated at temperatures above 75° C., including temperatures above the glass transition temperature of polymethylmethacrylate acrylic resin (Tg=105° C.), is t-butyl peroxybenzoate. Activation temperatures in the range of 75° C. to 200° C. can be used with t-butylperoxybenzoate and are often preferred.

The curing initiator can be used in amounts analogous to the amounts used in conventional acrylic-based molding compositions, which typically range from about 0.12 to 1.0 weight % of the molding composition, more typically about 0.3 to 1.0 weight %.

A critical element of the compositions of the present invention is the fiber reinforcement. These fibers are "long" fibers. The phrase "long fiber", as used herein, is intended to refer to those fibers having an aspect ratio, which is the ratio of fiber length to fiber diameter (L/D), that is theoretically large enough to result in fiber fracture near the midpoint when stressed. Long fibers comprised of conventional reinforcement materials have an aspect ratio exceeding 5:1. The lowest value for the aspect ratio at which this first occurs is referred to as the "critical aspect ratio." The critical aspect ratio defines the critical length at which a certain diameter fiber is considered "long". Fibers of different materials such as, for example, aramid, glass, graphite, etc., have different critical aspect ratios. In addition, identical fibers embedded in different matrices such as, for example, matrices of acrylic, epoxy, and polyester resins, have different critical aspect ratios. Examples of critical aspect ratios and critical lengths for various reinforcements and matrices are shown in Table 1 below.

TABLE 1

| Fiber | Matrix | (l/d)$_c$ | l$_c$ |
| --- | --- | --- | --- |
| E-Glass | Polypropylene | 140 | 1.78 mm |
| E-Glass | Epoxy | 34 | 0.43 |
| E-Glass | Polyester | 100 | 1.27 |
| Carbon | Epoxy | 47 | 0.33 |
| Carbon | Polycarbonate | 106 | 0.74 |

*Engineering Materials Reference Book, 2nd Ed., p. 77, Ed. Michael Bauccio, ASM International, 1994

The aspect ratio for fibers within a matrix comprised of a cured acrylic resin will be well above 5:1 for commercially available fiber reinforcements. Typically, the aspect ratio will be above 50:1 and it is often above 150:1. Conventional reinforcement fibers of glass, aramid, graphite, etc. having a length as low as 0.25 mm can function as long fibers within the compositions of this invention once cured since the fibers are thin and their aspect ratios are high.

While the lower limit for the preferred lengths of the long fibers is about 0.25 mm, the long fibers can be continuous, i.e. no measurable limit, when the molding composition is in the form of a sheet. The long fibers utilized in the molding doughs provided by this invention do have an upper limit for the preferred fiber lengths of about 6.5 mm. Preferred lengths for continuous fibers are at least 1 inch. Suitable types of fibers are 1) inorganic crystals or polymers, such as fibrous glass, quartz fibers, silica fibers and fibrous ceramics, which include alumina-silica (refractory ceramic fiber), boron fibers, silicon carbide whiskers or monofilament metal oxide fibers, including alumina-boria-silica, alumina-chromia-silica, zirconia-silica, and the like; 2) organic polymer fibers, such as fibrous carbon, fibrous graphite, acetates, acrylics (including acrylonitriles), aliphatic polyamides (e.g., nylons), aromatic polyamides, polyesters, flax, polyethylenes, polyurethanes (e.g., spandex), alpha-cellulose, cellulose, regenerated cellulose (e.g., rayon), jutes, sisals, vinyl chlorides, e.g., vinyon, vinyldienes (e.g., saran) and thermoplastic fibers; 3) metal fibers, such as aluminum, boron, bronze, chromium, nickel, stainless steel, titanium and their alloys; and 4) "Whiskers", which are single, inorganic crystals.

The reinforcing fibers preferably comprise such materials as glass, metals, carbon, rayon, cellulose acetate, cellulose triacetate and the like, Mylar™ polyester, aramid/Kevlar®, Nomex™ aramid fiber or polyethylene fiber in continuous or discontinuous form. A preferred fiber is silanized chopped glass fiber. The preferred length of fiber reinforcement utilized with the acrylic-based doughs such as bulk molding compounds (BMC), particularly Elvacite® 2051 bulk molding compounds, falls in the range of 0.25 to 6.5mm. The length of fiber reinforcement utilized with vinyl ester BIS-GMA doughs preferably ranges from 0. 1 to 6.5mm. Fibers can be used in an amount of from 10 wt. % up to about 90 wt. % for sheet materials. In dough molding compositions such as BMC, levels of fiber reinforcement above 25 wt. % show little advantage, although higher levels such as 50 wt % can be easily used. The dough molding compositions (BMC) preferably have at least 10 wt. % long fiber. Sheet molding compounds (SMC) can use discontinuous or continuous reinforcing fibers, filaments, braided, knit or woven fabrics.

A fiber reinforced composite is formed upon cure of the thermosetting molding compositions of the present invention. Where the thermosetting molding composition provides a composite with discontinuous fibers, the stress along the fiber is not uniform. There are portions along each fiber end where the tensile stresses are less than that of a fiber that is continuous in length. This region is often called the fiber ineffective length. The tensile stress along the fiber length increases to a maximum along the middle portion of the fiber. If the fiber is sufficiently long (critical length) so that the ratio of the length to diameter, or aspect ratio, equals or exceeds the critical aspect ratio, the mid-fiber stress will be equal to that of a continuous filament.

The critical aspect ratio which would result in fiber fracture at its mid-point can be expressed as $(l/d)_c = S_f/2Y$. Where $(l/d)_c$=the critical aspect ratio, l=length of the fiber and w=width of the fibers, $S_f$ is the tensile stress of the fiber and Y is the yield strength of the matrix in shear or the fiber-matrix interfacial shear strength, whichever value is lower.

If the fiber is shorter than the critical length, the stressed fiber will de-bond from the matrix and the composite will have low strength. When the length is greater than the critical length, the stressed composite will not de-bond the fibers and will exhibit high strength.

The rule of mixtures for discontinuous fiber composites may be expressed as $S_c = V_f \cdot S_f(1-l_c/2l) + V_m S_m$ where $S_c$ is the tensile strength of the composite, $S_m$ is tensile strength of the matrix, l is the actual length of the fiber, $l_c$ is the critical length of the fiber, $V_f$ is the volume fraction of the fiber and $V_m$ is the volume fraction of the matrix. For the composite to have a higher strength than its matrix, a minimum $V_f$ must be exceeded. This value may be 0.1 or greater for the plastic matrix composites. Because of high stress concentrations at the discontinuities that occur at the fiber ends, tensile strength of a discontinuous fiber composite will be from about 55% to 86% of the fiber tensile strength and the modulus can approach 90% to 95% of the corresponding continuous fiber composite.

The molding compositions of this invention can contain conventional additives where desired to obtain a particular additive effect either in processing or in the finished product. These include mechanical property modifiers, processing aids, surface property modifiers, physical property modifiers, electrical property modifiers, and conventional thickeners, such as Scott Bader's Crystig™ thickeners. Specific additives include anti-blocking agents, anti-caking agents, anti-foaming agents, antioxidants, anti-slip agents, anti-static agents, blowing agent, coupling agents, compatibilizers, dispersing aids, flatting agents, inhibitors, catalysts, accelerators/promoters, heat stabilizers, light stabilizers, wetting agents, plasticizers, extenders, thixotropics, flame, fire and smoke retarders, internal mold releases, lubricants, impact modifiers, tougheners, coloring/dyes/pigments, odorants and deodorants, low profile or low shrink additives, low pressure additives, clarifying agents, opacifiers, thickeners, viscosity control agents, permeability modifiers, biodegrading agents, flame retardants, foaming agents, blowing agents, solvents and waxes can be used. Conventional colorants can be used, such as dyes or pigments when necessary. In dental appliances, titanium dioxide and cadmium (peach colored) pigments are often used. The amount of colorant typically ranges from about 0.1–1.0 wt. % of the molding composition. Other suitable additives are dispersing agents, typically used in an amount of 1 to 8 wt. % of the molding compositions. An example of suitable dispersing agent is fumed silica sold under the trade name Cab-O-Sil®. Other additives include surfactants and mold release agents. Suitable mold release agents are stearate/ sterol alcohol and suitable surfactants are di-octylsulfosuccinate (sodium salt). The mold release agents are typically used in an amount of from 0.2–1.0 wt. % of the molding composition and the surfactants are used in the amount of 0.01 to 0.5 weight % of the molding composition.

Although the compositions of this invention contain fibers as reinforcement, it may still be desirable to add additional fillers, either inorganic or organic, to reduce shrinkage and distortion and improve the physical properties of the resulting composite. Preferred examples of inorganic fillers include silicate glass, fused silica, quartz and silanated glass ballotini. Others include calcium carbonates of various forms and origins, silica of various forms and origins, silicates, silicon dioxides of various forms and origins, clays of various forms and origins, calcium sulfates, micas, talcs, wood in various forms, glass (milled, platelets, spheres, micro-balloons) plastics (milled, platelets, spheres, microballoons), recycled polymer composite particles, metals in various forms, metallic oxides or hydroxides, metal hydrides or metal hydrates, carbon particles or granules, alumina (tabular), aluminum powder, aramid, bronze, carbon black, carbon fiber, cellulose, alpha cellulose, coal (powdered), cotton, fibrous glass, graphite, jute, molybdenum disulfide, nylon, orlon, rayon, silica (amorphous), sisal fibers, fluorocarbons, wood flour, kaolin, flax, zirconia and Feldspar. Although the more conventional metal oxide fillers such as magnesium oxide and calcium oxide do not inhibit the immediate physical properties of the resulting product and are suitable for the molding compositions of this invention, they do cause the molding compositions to thicken over time and therefore, molding compositions essentially free of these metal oxides thickeners are preferred. Metal oxide thickeners form ionic polymer networks with resin carboxyl groups requiring high pressure to break these bonds.

As to the organic fillers, the solid acrylic resin can function as a polymer filler when used as a thickener, but participates in the reaction unlike conventional fillers, an example being Elvacite® 2051(ICI) which is a thermoplastic polymethyl methacrylate free of benzoyl peroxide catalytic initiator. The organic fillers which do not react are typically used in an amount from about 0 to 30 wt. %, but compositions of this invention with preferred levels of organic fillers typically range from 0 to 20 wt. %, based on the total compound.

Compositions of this invention can be prepared using conventional mixing equipment such as a high shear blender. The components of the molding composition are preferably first combined into two separate portions, a liquid mixture portion and solid mixture portion. The liquid mixture includes the liquid monomer acrylic resin, oligomer or polymer (vinyl ester resin, or polyester resin) optionally surfactant and catalyst. The dry ingredients are mixed thoroughly in a high shear blender and typically include the solid acrylic polymer as filler, colorants, dispersing agents. Preferably, the reinforcing fibers are not blended into the solid mixture. Following preparation of the solid and liquid mixture portions, the two portions are combined in a low shear mixer for about five minutes, following which the reinforcing fibers are slowly added over an extended period. The fiber reinforcement is mixed so that there is no agglomeration of fibers and a uniform distribution is obtained by wetting these fibers. Once the fibers have been distributed throughout the liquid component, the mixture is allowed to stand (mature) for about two to five days with occasional stirring. This technique provides a bulk molding compound (BMC) consistent with the present invention. In forming sheet molding compounds (SMC), a mixture of liquid and solid components or a single component formulation are applied to a continuous fiber network of either knit, woven or braided fabrics or loose-lay filaments.

With the appropriate curing initiator blended therein, the thermosetting molding composition can be hardened by the application of heat or exposure to UV or visible light. The methods of this invention are suitable for preparing compositions with no polymerization initiator or with polymerization initiators that are active or inactive at ambient temperature. The vinyl ester resin blends are well suited for use with curing initiators that are activated by exposure to bright light. Of the heat cured resins, those which are activated at temperatures above 75° C. are preferred. Such temperatures are typically above the glass transition temperature of the acrylic resin which forms the matrix. The thermosetting molding compositions can be conveniently cured at temperatures of from 75° C. to 200° C. in an oil bath.

The compositions of this invention are well suited for producing dentures, inlays, crowns, bridge work, orthodontic devices, etc. However, these molding compositions are not confined to uses within the fields of dentistry (crowns, inlays), orthopedics (casts, splints) and podiatry. These compositions can be used in industrial applications such as model making and the production of utensils, automotive parts, bathroom fixtures and wherever enhanced physical properties must be combined with weatherability and ease of processing. The composition of this invention can be used in conventional matched die compression molding operations with conventional equipment or low compression molding operations, including low temperature cure techniques. The compositions of this invention can also be used in manual lay up applications in the fabrication of repair of articles. The composition can also be used as a purging compound to scour extruder barrels of molders and compounders.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius; and, unless otherwise indicated, all parts and percentages are by weight. In addition, unless otherwise indicated, all resin formulations are inhibited with trace amounts of either hydroquinone or methylethyl hydroquinone.

The disclosure of all patents and publications mentioned above and below and copending application Ser. No. 08/621, 723, filed Mar. 28, 1997, which will issue as U.S. Pat. No. 5,747,553 on May 5, 1998, are hereby incorporated by reference.

Protocol A

Stable, reinforced, thermoset, molding doughs of this invention were prepared according to the following protocol:

Phase 1: combine by TOTAL weight percent and mix separately as parts A and B:

Part A—The Liquid:

46 parts methylmethacrylate monomer;

8 parts ethylmethacrylate monomer;

4.5 parts ethyleneglycol dimethacrylate (cross-linker);

0.2 parts t-butyl peroxybenzoate (initiator);

0.1 parts dioctylsulfosuccinate, sodium salt (surfactant) and

A trace of methylethylhydroquinone (inhibitor).
Mix liquids thoroughly in a high shear blender, e.g. Lightin™ shear blender for 5 minutes.

Part B - The Powder:
1.0–8.% dispersing agent (Silica);
Colorants: TiO2, dyes and/or pigments;
33 parts Elvacite® 2051 (ICI);
5 parts Aramid PULP, no. 543; and
0.2 parts (peach) pigment.

Mix powders very thoroughly in a high shear blender for 5 minutes.

Phase 2: Combine liquid and powder by adding Part B, powder, to Part A, liquid, in a low shear mixer, e.g., Ross, Double Planetary machine, and mix for 45 minutes. Transfer to a sealed container and allow to stand (mature) for 1–4 days at 70° F. Occasional turning or stirring may be needed during maturation, depending on the formula, to incorporate free, liquid monomer.

The end product is a thick, pliable putty with a minimal tack.

Protocol B:

Stable, reinforced, thermoset, molding doughs of the present invention were prepared as follows:

Phase 1: Combine by weight and mix, separately, parts A and B:

Part A—The Liquid: A terpolymer resin mixture of:
70 grams methyl methacrylate resin;
20 grams ethyl methacrylate resin;
10 grams Bis-GMA vinyl ester resin, e.g., Nupol™ Bis-GMA vinyl ester resin 046-4005;
0.25 grams catalyst (t-butyl peroxybenzoate, or t-butyl hydro-peroxide, peroxy-ketals or VAZO™ catalyst);
0.14 grams di-octylsulfosuccinate (sodium salt), a surfactant.

Portion B—The Powder: Mix very thoroughly in a high shear blender:
5.0 grams silica dispersing agent;
0.4 grams Colorants: "Cadmium" pigment;
40.0 grams methylmethacrylate polymer filler, e.g., Elvacite™ 2051 methylmethacrylate polymer (ICI), which is free from benzoyl peroxide catalytic initiator;
6.0 grams fibrillated polyethylene, Short Stuff™ polyethylene, for mold lubrication, reduction of shrinkage and distortion, and to physically stabilize the suspension of the various powders in the mixture;
2.0 grams Calcium silicate (optional) to facilitate processing;
20.0 grams silanated, glass ballotini.

Weigh out, but do not mix in high shear blender,
25.0 grams Reinforcing fibers: glass, metals, carbon, nylon, aramid fiber (KEVLAR®), especially in its fibrillated forms, e.g., DuPont's 540–543 aramid fiber (KEVLAR®) pulp, or, Nomex® aramid fiber.

Phase 2:
1) Place 75 grams of Portion A—The Liquid in a low shear mixer, add Portion B—The Powder and mix slowly and thoroughly for 5 minutes.
2) Slowly add 25.0 grams of silanated, chopped glass fiber and continue to mix for 15 minutes.

Cover the mix in a sealed container and allow to stand (mature) for 2–4 days. Occasional stirring or turning may be needed, depending on the formula, to incorporate free liquid resin.

The end product is a thick, pliable putty with a minimal tack.

A typical bulk molding formulation is as follows:

|  | wt. % |
|---|---|
| solid acrylic | 26 |
| liquid monomer | 2.5 |
| calcium carbonate | 50 |
| zinc stearate (mold release) | 1 |
| t-butyl peroxide benzoate | .5 |
| glass fibers (1/4 in) | 20 |

Sheet molding compound is composed of basically four principle ingredients: the thermosetting components (liquid monomer, oligomer or polymer, and solid acrylic resin), fiber reenforcement, additives and fillers. It is feasible to use various types of specific ingredients for each of the four principle ingredients such that an almost indefinite number of formulations are possible.

In the compounding process for SMC formulations, the ingredients are mixed together in two different batches, most commonly referred to as Part A and Part B. Part B includes the solid acrylic resin as its prime ingredient; the additives and fillers act as carriers. Part A includes the liquid monomer, except the glass fibers. Parts A and B are pumped separately at a predetermined ratio and are mixed completely to form the final paste immediately prior to loading the doctor box. This ratio is normally maintained in the range 1:1 to 20:1 to obtain the best metering, as well as mixing of ingredients. The paste is then applied to two carrier films to form a sandwich layer with glass fibers in the middle.

The compounded sheets are then stored to age in a controlled environment. The maturation period (normally 2 to 5 days) is, in effect, the time needed for the paste viscosity to reach a level sufficient for molding. The paste viscosity at the time of compound is typically below 40,000 cps (mPa·s), whereas at the time of molding, the viscosity is preferably $20 \times 10^6$ to $30 \times 10^6$ cps.

| SMC Formulation with Thermoplastic Resin | | |
|---|---|---|
| SMC Paste | Part by Wt. | Range |
| Solid acrylic resin | 60 | 15–25 |
| Liquid monomer | 100 | 20–25 |
| Thermoplastic resin | 40 | 5–12 |
| Calcium carbonate (3–5 μm particle size) | 150 | 20–40 |
| t-butyl peroxybenzoate | 1.5 | |
| Zinc stearate (mold release) | 4.0 | |
| Fiber glass - Chopped (1 inch) | 125 | 20–40 |

EXAMPLES 1–4

Bulk molding compounds of this invention prepared in accordance with Protocol A. The components of these molding compounds are shown in the Table below:

| Example No. | 1 | 2 | 3 | 4 |
|---|---|---|---|---|
| INGREDIENT & Weight Percent | Unreinforced Dough Vehicles: | | | |
| Resin, Liquid | | | | |
| Methyl methacrylate | 61.00% | | 30.50% | |

-continued

| Example No. | 1 | 2 | 3 | 4 |
|---|---|---|---|---|
| Ethyl methacrylate | | 61.00% | 30.50% | |
| Other Acrylic Resins or Copolymers | | | | 63.00% |
| Reinforcement | | | | |
| Mineral Filler | | | | |
| Organic Filler | | | | |
| Coupling Agent | | | | |
| Internal Mold Release Agent | | | | |
| Colorant | | | | |
| Curing Agent(s) | | | | |
| t-butyl peroxybenzoate | 0.30% | 0.30% | 0.30% | 0.30% |
| Thickener | | | | |
| Cab-O-Sil, fumed silica | 2.00% | 2.00% | 2.00% | 2.00% |
| Acrylic Polymer Powder* | 36.70% | 36.70% | 36.70% | 34.70% |
| Low Profile Additive: | | | | |
| Any & All additives must be Benzoyl Peroxide (BPO) free. | | | | |

*All thickening and/or polymer powder is benzoyl peroxide free. Example: ICI's, Elvacite 2051, or, Elvacite 2697.

EXAMPLES 5–8

Examples 5–8 describe bulk molding compounds of this invention prepared in accordance with protocol A. The components of the molding compounds are shown in the Table below.

| Example No.: | 5 | 6 | 7 | 8 |
|---|---|---|---|---|
| INGREDIENT & Weight Percent | | | | |
| Resin, Liquid | | | | |
| Methyl methacryate | 43.11% | 35.00% | 40.00% | |
| Ethyl methacrylate | | 8.11% | 8.10% | |
| Other Acrylic Resins or Copolymers | | | | 52.05% |
| Reinforcement | | | | |
| Glass Fiber | 15.00% | 15.00% | | |
| Others** | | | 15.00% | 15.00% |
| Mineral Filler | | | | |
| Silica | | | | |
| Glass/Quartz | 20.00% | 20.00% | 9.00% | |
| Feldspar | | | 5.00% | |
| Organic Filler | | | | 13.00% |
| (Example: Powdered polyethylenes) | | | | |
| Coupling Agent | | | | |
| Silane | 2.00% | 2.00% | 2.00% | 2.00% |
| Internal Mold Release Agent | | | | |
| (Example: Magnesium stearate) | | | | |
| Colorant | 0.30% | 0.30% | 0.30% | 0.30% |
| Curing Agent(s) | | | | |
| t-butyl peroxybenzoate | 0.25% | 0.25% | 0.30% | 0.30% |
| Azo-FRS (DuPont VAZO Catalysts) | | | | |
| Peroxyester | | | | |
| Peroxy Ketal | Other Possible Catalysts | | | |
| Thickener | | | | |
| Acrylic Polymer Powder | 17.34% | 17.34% | 15.35% | 15.35% |
| Silica | 2.00% | 2.00% | 2.00% | 2.00% |
| Low Profile Additive: | | | | |
| Polyethylene Powder or Pulp | | | | 3.00% |

**Includes those selected from metal fibers and flakes, phosphate fiber, Wallostonite, Dawsonite, Micro Fiber glass, processed mineral fiber, TISMO (old Fibex), magnesium oxysulfate fiber (MOS)
NOTE: Reinforcements and fillers are so numerous that they cannot be specifically named.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of preparing a shelf-stable molding composition which comprises:
   a) mixing a solid acrylic resin, which is free of active free-radical polymerization initiators, with
      (i) one or more liquid monomers, liquid oligomers, liquid polymers or a combination thereof with vinyl unsaturation, which polymerizes in the presence of an activated free-radical polymerization initiator, wherein said solid acrylic resin absorbs said liquid monomers, liquid oligomers, liquid polymers and combinations thereof, and reacts with said liquid monomers, liquid oligomers, liquid polymers and combinations thereof, in the presence of an activated free-radical polymerization initiator; and
      (ii) long fiber reinforcement having an aspect ratio L/D greater than 5:1, which is insoluble in said solid acrylic resin; and
   b) aging the mixture of solid acrylic resin, and liquid monomers, liquid oligomers, liquid polymers or combinations thereof, and long fiber reinforcement for at least 24 hours to allow absorption of the liquid monomer, liquid oligomer, liquid polymer or combination thereof containing vinyl unsaturation, by the solid acrylic resin.

2. A method as in claim 1, wherein said long fiber reinforcement is of a length at least about 0.25 mm and the particle size of the solid acrylic resin falls within the range of 0.005 mm to 0.5 mm.

3. The method as in claim 1 comprising the additional step of mixing a free-radical polymerization initiator with said mixture of solid acrylic resin, liquid monomers, oligomers, polymers or combination thereof containing vinyl unsaturation, and long fiber reinforcement.

4. A method as in claim 3, wherein the free-radical polymerization initiator is inactive at ambient temperature or its activity can be restrained under ambient conditions.

5. A method as in claim 3 comprising the additional step of heating the solid acrylic resin before mixing to inactivate any free radical polymerization initiators therein.

6. A method as in claim 3, wherein the free-radical polymerization initiator is selected from the group consisting of ketone peroxides, alkyl peroxides, aryl peroxides, peroxy esters, perketals, peroxydicarbonates, alkylhydroperoxides, diacyl peroxides, VAZO compounds, photoinitiators and heat labile photoinitiators.

7. A method as in claim 4, wherein the free-radical polymerization initiator is activated by exposure to UV light, visible light or a temperature greater than 75° C.

8. A method as in claim 1 which comprises a solid acrylic resin selected from the group consisting of linear homopolymers, copolymers or block copolymers of acrylate or methacrylate monomers and the liquid monomer is selected from acrylic monomers, methacrylic monomers, styrene monomers and the liquid oligomers is selected from acrylic oligomers, methacrylic oligomers, styrene oligomers, vinyl ester oligomers and polyester oligomers.

9. A method as in claim 1, wherein the liquid monomer is selected form the group consisting of acrylic acid monomers, methacrylic acid monomers, acrylate monomers, methacrylate monomers, vinyl ether monomers, acrylonitrile monomers, propylene monomers, vinyl acetate monomers, vinyl alcohol monomers, vinyl chloride monomers, vinylidine chloride monomers, butadiene monomers, isobutadiene monomers, isoprene monomers, divinyl benzene and mixtures thereof.

10. A method as in claim 1, wherein said fiber reinforcement is selected from the group consisting of glass fibers, carbon fibers, metal fibers, rayon fibers and organic polymer fibers.

11. A method as in claim 1, wherein the solid acrylic resin absorbs 90% of said liquid monomers, oligomers, polymers or combination thereof, in a period of two hours or more.

12. A method as in claim 1, wherein the long fiber reinforcement comprises 15 wt. % to 50 wt. % of the total composition.

13. A method as in claim 1, wherein the viscosity of the composition increases with absorption by the solid acrylic resin of at least 90% of the liquid monomers, liquid oligomers, liquid polymers or combination thereof, and substantial viscosity build is delayed for at least two hours after the solid acrylic polymer is mixed with the liquid monomer, liquid oligomer, liquid polymer or combinations thereof.

14. A method as in claim 13, wherein the absorption of at least 90% of the liquid monomers, oligomers, polymers or combination thereof, by the solid acrylic resin is complete in 1 to 4 days from mixing the solid acrylic polymer with the liquid monomers, liquid oligomers, liquid polymers or combinations thereof.

15. A composition which comprises:
 a) a liquid monomer, liquid oligomer, liquid polymer or combination thereof with vinyl unsaturation, which polymerizes in the presence of an activated free-radical polymerization initiator;
 b) at least 35 wt. % based on the total weight of the liquid monomer, liquid oligomer, liquid polymer or combination thereof in the composition, of a solid acrylic resin which is soluble in said liquid monomer, liquid oligomer, liquid polymer or combination thereof containing vinyl unsaturation, having an average particle size in the range of 0.005 mm to 0.5 mm with at least a portion of said liquid monomer, liquid oligomer, liquid polymer or combination thereof containing vinyl unsaturation, absorbed therein, which is free of active free-radical polymerization initiators and which reacts with the liquid monomer, liquid oligomer, liquid polymer or combination thereof containing vinyl unsaturation, absorbed therein in the presence of an activated free-radical polymerization initiator;
 c) at least 10 wt. %, based on the total weight of the composition, of long fiber reinforcement having an aspect ratio (L/D) greater than 5:1 and an average length of at least 0.25 mm which is insoluble in the solid acrylic resin; and
 d) a free-radical polymerization initiator, the activity of which can be restrained under ambient conditions or is inactive at ambient temperature so as to provide a shelf life of at least one month at ambient temperature, wherein said composition is free of alkali earth metal oxide fillers.

16. A composition as in claim 15, wherein the free radical initiator is selected from the group consisting of:
 ketone peroxides
 alkyl peroxides
 aryl peroxides
 peroxy esters
 perketals
 peroxydicarbonates
 alkylhydroperoxides
 diacyl peroxides
 VAZO compounds
 photoinitiators and
 heat labile photoinitiators.

17. A thermosetting molding composition as in claim 15, wherein the free-radical polymerization initiator is activated by exposure to ultraviolet light, visible light or a temperature above 75° C.

18. A composition as in claim 15, wherein the particles of solid acrylic polymer have an average size of about 0.1 mm.

19. A composition as in claim 15, wherein the amount of solid acrylic resin within the molding composition ranges from 35 to 70 wt. %, based on the total weight of liquid monomer, oligomer, polymer or combination thereof in said composition.

20. A composition as in claim 15 which comprises a solid acrylic resin selected from the group consisting of linear homopolymers, copolymers or block copolymers of acrylate or methacrylate monomers and the liquid monomer is selected from acrylic monomers, methacrylic monomers, styrene monomers and the liquid oligomer is selected from acrylic oligomers, methacrylic oligomers, styrene oligomers, vinyl ester oligomers and polyester oligomers.

21. A composition as in claim 15, wherein the liquid monomer is selected from the group consisting of acrylic acid monomers, methacrylic acid monomers, acrylate monomers, methacrylate monomers, vinyl ether monomers, acrylonitrile monomers, propylene monomers, vinyl acetate monomers, vinyl alcohol monomers, vinyl chloride monomers, vinylidine chloride monomers, butadiene monomers, isobutadiene monomers, isoprene monomers, divinyl benzene and mixtures thereof 22. A composition as in claim 15 in the form of a bulk molding compound having a viscosity suitable for molding at the temperatures and pressure employed in low pressure molding equipment, wherein said long fiber reinforcement has an average length of at least 1 mm and comprises from 15 to 50 wt. % of the total molding composition.

23. A molding composition as in claim 15 in the form of a sheet molding compound having a viscosity suitable for molding at the temperatures and pressures employed in low pressure molding equipment, wherein said long fiber reinforcement has a length greater than 1 inch and comprises from 25 to 70 wt. % of the total molding composition.

24. A composition as in claim 15, wherein said fiber reinforcement is selected from the group consisting of glass fibers, carbon fibers, metal fibers, rayon fibers and organic polymer fibers other than acrylic resin fibers.

25. A composition as in claim 15, wherein at least 90% of said liquid monomer, liquid oligomer, liquid polymer or combination thereof, is absorbed by said solid acrylic resin.

26. A composition as in claim 15, wherein the long fiber reinforcement comprises 15 wt. % to 50 wt. % of the total composition.

27. A composition which comprises:
 a) a liquid monomer, liquid oligomer, liquid polymer or combination thereof containing vinyl unsaturation which polymerizes in the presence of an activated free-radical polymerization initiator;
 b) 35–70 wt. %, based on the total weight of the liquid monomer, liquid oligomer, liquid polymer or combination thereof in the composition, of a solid acrylic resin which is soluble in said liquid monomer, liquid oligomer, liquid polymer or combination thereof containing vinyl unsaturation, which has an average particle size in the range of 0.005 mm to 0.5 mm, which has at least a portion of said liquid monomer, liquid oligomer, liquid polymer or combination thereof containing vinyl unsaturation absorbed therein, and which is free of free-radical polymerization initiators;

c) at least 10 wt. % based on the total weight of the composition of long fiber reinforcement having an aspect ratio (L/D) greater than 5:1 and an average length of at least 0.25 mm, wherein said composition is shelf stable for at least one month and is free of alkali earth metal oxide fillers and active free-radical polymerization initiators.

28. A composition as in claim 27, wherein the long fiber reinforcement comprises 15 wt. % to 50 wt. % of the total composition.

29. A composition which comprises:
   a) a liquid monomer with vinyl unsaturation which cures to a thermoset resin in the presence of an activated free-radical polymerization initiator;
   b) at least 35 wt. %, based on the total weight of the liquid monomer in the composition, of a solid acrylic resin which is essentially free of active free-radical polymerization initiators;
   c) at least 10 wt. %, based on the total weight of the composition, long fiber reinforcement having an aspect ratio (L/D) greater than 5:1; and
   d) a free-radical polymerization initiator selected from the group consisting of ketone peroxides, alkyl peroxides, aryl peroxides, peroxy esters, perketals, peroxy dicarbonates, alkyl hydroperoxides, diaryl peroxides, VAZO compounds, photoinitiators and heat labile photoinitiators.

30. A composition as in claim 29 which additionally comprises a solid resin, other than a solid acrylic resin, which polymerizes in the presence of an activated free-radical polymerization initiator.

* * * * *